(12) United States Patent
Lignell et al.

(10) Patent No.: US 6,335,015 B1
(45) Date of Patent: Jan. 1, 2002

(54) METHOD OF THE PROPHYLACTIC TREATMENT OF MASTITIS

(75) Inventors: Ake Lignell; Johan Inborr, both of Varmdo (SE)

(73) Assignee: Astacarotene AB, Gustavsberg (SE)

( * ) Notice: Subject to any disclaimer, the term of this patent is extended or adjusted under 35 U.S.C. 154(b) by 0 days.

(21) Appl. No.: 09/589,594

(22) PCT Filed: Dec. 10, 1998

(86) PCT No.: PCT/SE98/02279

§ 371 Date: Jul. 25, 2000

§ 102(e) Date: Jul. 25, 2000

(87) PCT Pub. No.: WO99/30701

PCT Pub. Date: Jun. 24, 1999

(30) Foreign Application Priority Data

Dec. 16, 1997 (SE) .............................................. 9704693

(51) Int. Cl.⁷ ................................................ C12P 23/00
(52) U.S. Cl. ............... 424/195.1; 424/725; 424/195.17; 435/67
(58) Field of Search .................................. 514/725, 763; 424/538, 581, 195.1, 234.1, 274.1, 823, 439, 725, 763; 435/67, 234.1

(56) References Cited

FOREIGN PATENT DOCUMENTS

| | | | |
|---|---|---|---|
| EP | 0770385 A | | 5/1997 |
| JP | 02049091 A | | 2/1990 |
| SE | 9300901-7 A | | 9/1994 |
| WO | WO 9623489 A | | 8/1996 |
| WO | WO 97/35491 | * | 10/1997 |
| WO | WO 9735491 A | | 10/1997 |

* cited by examiner

*Primary Examiner*—Leon B. Lankford, Jr.
*Assistant Examiner*—Ruth A. Davis
(74) *Attorney, Agent, or Firm*—Bacon & Thomas

(57) ABSTRACT

A method of prophylactic treatment of mastitis in mammalian, including human, mothers, is described. The method comprises administration of a prophylactically effective dosage of a human or veterinary medicament containing at least one type of xanthophylls, such as astaxanthin, to said mothers. Preferably, the astaxanthin exists in a form esterified with fatty acids, e.g. in the form of algae meal produced by culturing of the alga Haematococcus sp. Further, use of at least one type of xanthophylls, such as astaxanthin, for the preparation of a human or veterinary medicament for the prophylactic treatment of mastitis is mammalian, including human, mothers is disclosed.

5 Claims, No Drawings

METHOD OF THE PROPHYLACTIC TREATMENT OF MASTITIS

The present invention relates to a method of the prophylactic treatment of mastitis of mammalian, including human, mothers. The method comprises administration of a prophylactically effective dosage of a human or veterinary medicament containing at least one type of xanthophylls, such as astaxanthin, to the mothers. The invention also relates to the use of at least one type of xanthophylls, such as astaxanthin, for the preparation of a human or veterinary medicament for the prophylactic treatment of mastitis.

BACKGROUND

Mastitis (inflammation of the mammary gland) is a commonly appearing and often painful disease in both human and animal mothers during the breast feeding/suckling period as well as during the lactation period. The primary cause is usually a bacterial infection. Physical damage to the breasts, udder or the teats may predispose the individual to such infections. Further, mastitis can dramatically reduce milk production, which results in reduced nutrient and immunoglobulin intake by the offspring and/or reduced income for the dairy farmer. Therapeutic treatment usually involves medication, and consultation of a doctor/veterinarian, which is expensive.

Ingestion of mother's milk is of crucial importance for the growth and health status of the new born mammal. The milk is the primary source of energy, proteins, fat and other essential nutrients during the breast feeding/suckling period. In addition, in dairy farming, the level of milk production and yields are of great importance for the profitability of the farmer. In summary, any reduction in milk production will have serious economic and health consequences.

Our published International patent application WO 97/35491 relates to an agent for increasing the production of/in breeding and production mammals, and discloses experiments wherein sows were given feed supplemented with astaxanthin during a period prior to parturition and during lactation resulting in e.g. more piglets born alive.

Astaxanthin, and other xanthophylls, are known to exhibit antioxidative properties, and hence possess the ability to scavenge so-called free radicals. However, in biological tests astaxanthin has been shown to possess clearly the best antioxidative properties compared to other carotenoids (Miki W., 1991, Pure and Appl Chem 63 (1): 141–146).

DESCRIPTION OF THE INVENTION

The present invention is directed to a method of prophylactic treatment of mastitis in mammalian, including human, mothers, comprising administration of a prophylactically effective dosage of a human or veterinary medicament containing at least one type of xanthophylls to said mothers.

In a preferred embodiment the type of xanthophylls is astaxanthin. In a particularly preferred embodiment the astaxanthin exists in a form in which it is esterified with fatty acids. The last mentioned form of astaxanthin may be in the form of algal meal produced by culturing of the alga Haematococcus sp.

A prophylactically effective dosage of the preparation contains e.g. 0.01 to 1 mg astaxanthin per kg body weight per day.

The invention is also directed to the use of at least one type of xanthophylls for the preparation of a human or veterinary medicament for the prophylactic treatment of mastitis in mammalian, including human, mothers.

Here again, in a preferred embodiment the type of xanthophylls is astaxanthin. In a particularly preferred embodiment the astaxanthin exists in a form in which it is esterified with fatty acids. The last mentioned form of astaxanthin may be in the form of algal meal produced by culturing of the alga Haematococcus sp.

For example, the amount astaxanthin in the medicament is 0.01 to 1 mg per body weight of the human or animal mother.

In the present invention the human and veterinary medicaments may comprise a mixture of different types of xanthophylls or different forms of the same xanthophyll, such as a mixture of synthetic astaxanthin and naturally produced astaxanthin.

The human and veterinary medicament of the invention may comprise additional ingredients which are pharmacologically acceptable inactive or active, such as flavoring agents, excipients, diluents, carriers, etc., and it may be presented in a separate unit dose or in admixture with food or feed. Examples of separate unit doses are tablets, gelatin capsules and predetermined amounts of solutions, e. g. oil solutions, or emulsions, e.g. water-in-oil or oil-in-water emulsions. Examples of food in which the preparation of the invention may be incorporated is dairy products, such as yogurt, chocolate and cereals.

DESCRIPTION OF EXPERIMENTED

The medicament used in the experiments contained the xanthophyll astaxanthin which was produced via the alga Haematococcus sp. by AstaCarotene AB, Gustavsberg, Sweden.

Naturally produced astaxanthin can be obtained also from fungi and crustaceans, in addition to from alga. Astaxanthin from other sources, and other xanthophylls as well, are expected to be similarly useful for the purposes of the invention. An advantage of using astaxanthin from alga is, however, that the astaxanthin exists in a form esterified with fatty acids [Renström B. et al, 1981, Phytochem 20(11): 2561–2564], which esterified astaxanthin thereby is more stable during handling and storage than free astaxanthin.

EXPERIMENTAL DESIGN AND RESULTS

A group of 120 dairy cows with a known record of milk production and incidence of mastitis from the previous lactation period were given algal meal (from *Haematococcus pluvialis*) to provide 100 mg natural astaxanthin per day during a period extending from parturition to 12 weeks thereafter.

During this period only one incidence of mastitis was recorded. This number should be compared to 8 cases recorded in the same cows during the previous lactation period.

Milk production was 6higher in the current period (100 mg natural astaxanthin/day/cow) compared to the previous one (no natural astaxanthin).

What is claimed is:
1. Method of prophylactic treatment of mastitis in human mothers, comprising administration of a prophylactically effective dosage of a human medicament containing at least one type of xanthophylls to said mothers.
2. Method according to claim 1, wherein the type of xanthophyll is astaxanthin.
3. Method according to claim 2 wherein the astaxanthin exists in a form esterified with fatty acids.
4. Method according to claim 3 wherein the esterified astaxanthin is in the form of algal meal produced by culturing of the alga Haematococcus sp.
5. Method according to claim 4 wherein the effective dosage of the medicament contains 0.01 to 1 mg astaxanthin per kg body weight per day.

* * * * *